United States Patent [19]
Schouwenburg

[11] Patent Number: 6,159,243
[45] Date of Patent: Dec. 12, 2000

[54] KIT FOR IMPLANTATION OF A VOICE PROSTHESIS IN PATIENTS ON WHOM A LARYNGECTOMY HAS BEEN PERFORMED

[76] Inventor: Paul Ferdinand Schouwenburg, Grenslaan 4, NL-2111 GH Aerdenhout, Netherlands

[21] Appl. No.: 09/180,388
[22] PCT Filed: Mar. 10, 1997
[86] PCT No.: PCT/NL97/00118
 § 371 Date: Apr. 6, 1999
 § 102(e) Date: Apr. 6, 1999
[87] PCT Pub. No.: WO97/41807
 PCT Pub. Date: Nov. 13, 1997

[30] Foreign Application Priority Data

May 6, 1996 [NL] Netherlands ............................ 1003043

[51] Int. Cl.[7] ........................................................ A61F 2/20
[52] U.S. Cl. ................................................. 623/9; 606/108
[58] Field of Search ................................. 623/9; 604/194, 604/196, 193, 174, 171; 128/200.26, 207.29; 606/108

[56] References Cited

U.S. PATENT DOCUMENTS

| | | |
|---|---|---|
| 5,078,743 | 1/1992 | Mikalov et al. . |
| 5,084,014 | 1/1992 | Picha et al. . |
| 5,257,636 | 11/1993 | White ............................. 128/200.26 X |
| 5,571,180 | 11/1996 | Blom ........................................... 623/9 |
| 5,728,068 | 3/1998 | Leone et al. ......................... 606/108 X |
| 5,735,817 | 4/1998 | Shantha ............................... 604/194 X |
| 5,976,151 | 11/1999 | Siegbahn ................................. 606/108 |

FOREIGN PATENT DOCUMENTS

| | | |
|---|---|---|
| 8302122 | 1/1985 | Netherlands . |
| 29649 | 11/1995 | WIPO . |

Primary Examiner—Michael J. Milano
Assistant Examiner—Brian E Pellegrino
Attorney, Agent, or Firm—Sughrue, Mion, Zinn, Macpeak & Seas, PLLC

[57] ABSTRACT

A voice prosthesis implantation kit includes a leader element which can be introduced via the mouth into the oesophagus until the leading end or tip of the leader element is located close to the location where the voice prosthesis has to be implanted, at which tip of the leader element a first coupling device is located. The kit also includes a hollow cutting element for making a cut in the wall of the oesophagus at the level of the tracheostome, and a guide element, one end of which carries a second coupling device which, via the hollow cutting element which is located in the cut which has been made, can be brought into interaction with the first coupling device, and the other end of which carries an attachment for a voice prosthesis, which is to be implanted, to the guide element.

8 Claims, 3 Drawing Sheets

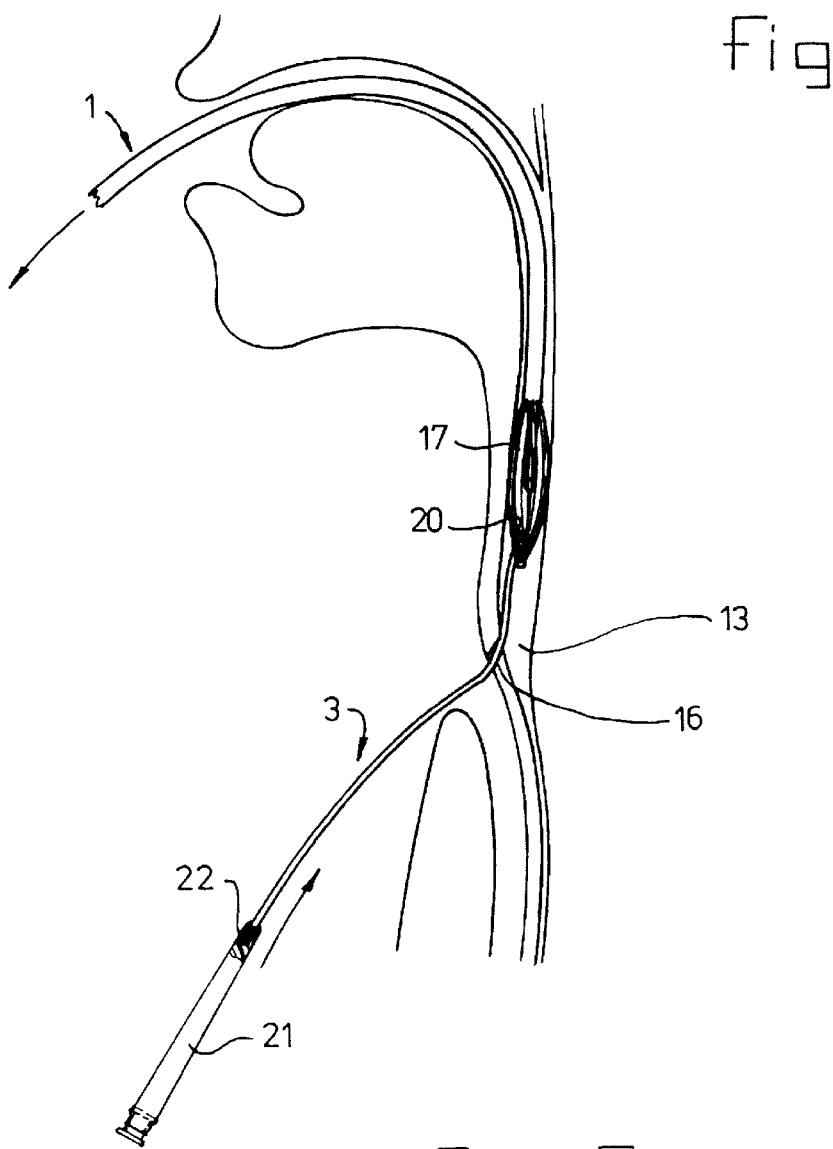
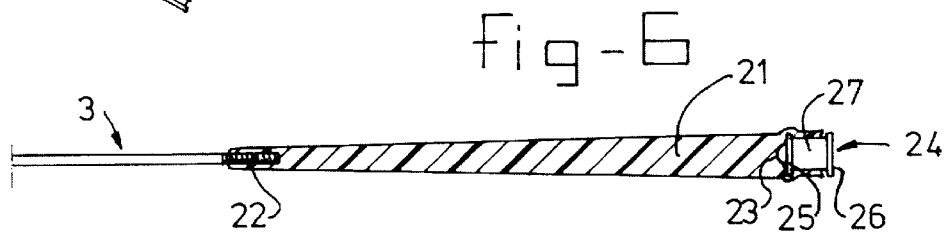
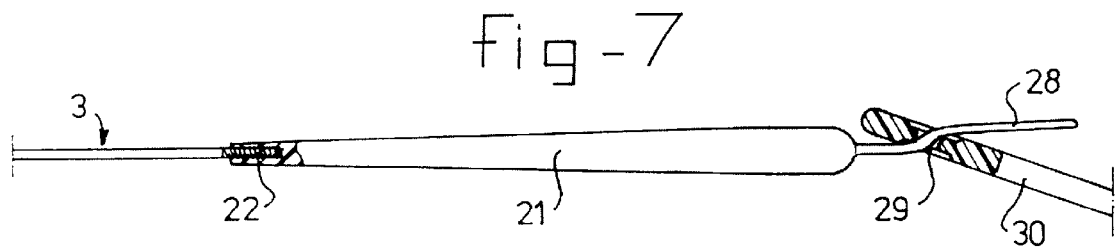

KIT FOR IMPLANTATION OF A VOICE PROSTHESIS IN PATIENTS ON WHOM A LARYNGECTOMY HAS BEEN PERFORMED

BACKGROUND OF THE INVENTION

This invention relates to the implantation of voice prostheses to restore the voice in patients on whom a laryngectomy has been performed or patients who have no vocal cords, in particular but not exclusively by means of a secondary tracheo-oesophageal puncture. A secondary puncture of this type is employed if the voice prosthesis is implanted only some time after the laryngectomy has been carried out. This is in contrast to the primary puncture, according to which the voice prosthesis is implanted immediately after the laryngectomy.

According to the traditional treatment method, the patient is placed under general anaesthesia for the secondary puncture, which necessitates the patient spending a few days in the hospital as an in-patient. This treatment method is consequently fairly time-consuming and involves relatively high costs.

SUMMARY OF THE INVENTION

The aim of the invention is to simplify the post-laryngectomy implantation of voice prostheses by means of a secondary puncture. This aim is achieved by means of a kit for the implantation of a voice prosthesis to restore the voice in a patient on whom a laryngectomy has been performed, comprising:

- a leader element which can be introduced via the mouth into the oesophagus until the leading end or tip of the leader element is located close to the location where the voice prosthesis has to be implanted, at which tip of said leader element coupling means are located,
- a hollow cutting element for making a cut in the wall of the oesophagus at the level of the tracheostome, and
- a guide element, one end of which carries coupling means which, via the hollow cutting element which is located in the cut which has been made, can be brought into interaction with the coupling means at the tip of the leader element, and the other end of which carries attachment means for attaching a voice prosthesis, which is to be implanted, to the guide element.

With the aid of a kit of this type the patient can be treated without general anaesthesia being necessary. Instead of the latter, the patient is locally anaesthetised by means of local and infiltration anaesthesia of tracheostome and oesophagus. The leader element is then introduced, after which the cut is made, by means of the hollow cutting element or trocar, to form an opening in the tracheo-oesophageal wall in which the voice prosthesis has to be implanted.

Via the cut made in this way it is possible, if appropriate after removing the cutting part of the trocar, to couple the guide element to the coupling means of the leader element. By then withdrawing the leader element together with the guide element, which has now been coupled up, the voice prosthesis attached to said guide element can be implanted directly in the opening, the cut concerned being widened at the same time.

Finally, the attachment between prosthesis and guide element can be released by pulling free and withdrawing the guide element via the mouth. Implantation of the voice prosthesis is thus complete.

Successful performance of the abovementioned operation is highly dependent on making the cut in the correct manner, that is to say as soon as the tip of the leader element is at the location desired for the voice prosthesis. With a view to simplifying these activities, the leader element preferably has a light source close to its tip. The light source is detectable through the tracheo-oesophageal wall, so that it is possible to establish immediately whether the tip of the leader element is in the correct position, immediately behind the region where the cut will be made.

Contact with the rear wall of the oesophagus must, of course, be avoided when making the cut in the tracheo-oesophageal wall. Since the oesophagus is usually flat, the risk that the trocar nevertheless unintentionally comes into contact with the rear wall is fairly high. This risk can be appreciably reduced by means of a construction wherein the leader element comprises an expansion element which carries the coupling means for coupling to the guide element.

In the expanded state, the expansion element produces a certain cavity in the oesophagus, such that the trocar can be inserted without the oesophagus being damaged.

An expansion element of this type can be constructed in various ways. Preference is for a construction wherein the expansion element is a balloon which can be inflated via a tube provided in the leader element. The balloon can have a cage or grid of reinforcing threads or wires.

The coupling means can also be constructed in a variety of ways. A particular embodiment which is particularly suitable for use with an expansion element in balloon form comprises a guide element which carries barb-shaped coupling means which are folded together on insertion into the trocar, which coupling means can be inserted in the balloon via the trocar and can then fold out such that they remain hooked into the balloon and/or the cage or the grid.

A further advantage of the expansion element in balloon form is that the non-expanded state can easily be restored by allowing said balloon to deflate completely via the associated tube, or by pricking an opening in said balloon using the trocar.

In order to be able to implant the voice prosthesis immediately after the cut has been made in the tracheo-oesophageal wall, a dilator is provided which at one end is connected to the guide element and at the other end has attachment means for a voice prosthesis for widening the cut when implanting a voice prosthesis attached to the dilator.

Said dilator can be in the shape of a cone, the apex of which is connected to the guide element.

BRIEF DESCRIPTION OF THE DRAWINGS

The invention will be explained in more detail below with reference to an illustrative embodiment shown in the figures.

FIG. 5 shows part of the kit according to the invention when implanting the prosthesis.

FIGS. 6 and 7 show various dilators.

DETAILED DESCRIPTION OF THE DRAWINGS

Figure 1:
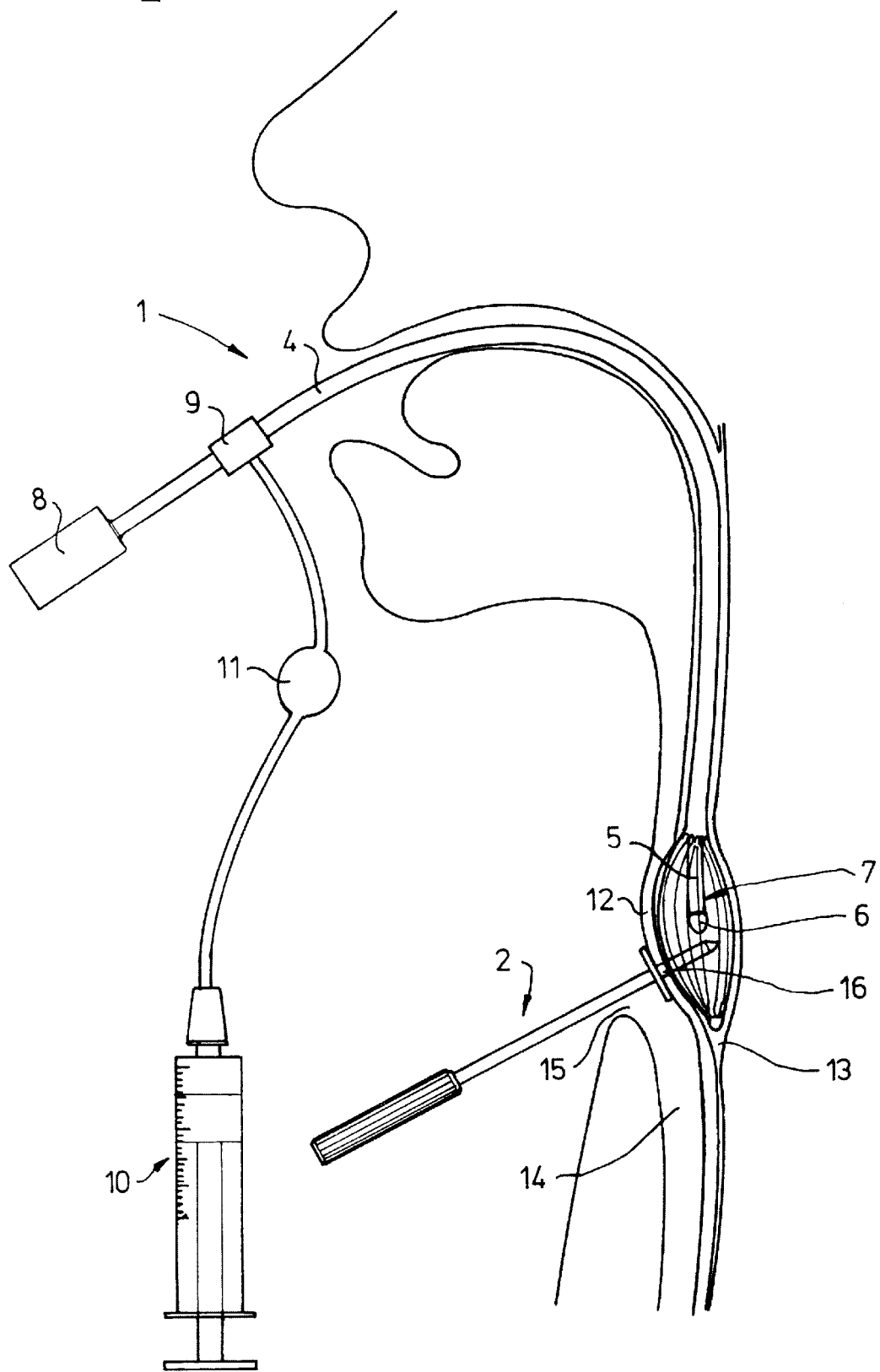
FIG. 1 shows the kit according to the invention, after it has been introduced.

The kit for the implantation of a voice prosthesis to restore the voice in patients on whom a laryngectomy has been performed, which is shown in FIG. 1, comprises a leader element, which is indicated in its entirety by 1, and a cutting element 2. The third element in the kit according to the invention, the guide element 3, is shown in FIG. 5.

The leader element 1 comprises a flexible tube 4, through the inside of which a power supply cable 5 for a light source 6 runs. Said power supply cable 5 with light source 6 emerges at that end of the flexible tube 4 which is introduced into the oesophagus 13. An expansion element, which is indicated in its entirety by 7, or balloon 18, is also fitted on said end.

A power source 8, to which the power supply cable 5 for the light source 6 is connected, is provided at the other end of the flexible tube 4. Furthermore, a pumping element 10, which in the case shown is an injection syringe, is coupled close to said end by means of coupling 9. A bellows 11, by means of which the size of the expansion element 7 can be controlled, is located between coupling element 9 and injection syringe 10.

The expansion element 7 is in the retracted state while the leader element 1 is being introduced. By means of the light source 6 it is possible accurately to check the position of expansion element 7. As soon as the correct position has been reached, as is shown in FIG. 1, introduction is discontinued and the expansion element 7 is expanded by pumping air into the latter using injection syringe 10 and, if necessary, bellows 11. The oesophagus widens as a result, such that space is created to enable a hole to be made safely in the wall 12 between oesophagus 13 and trachea 14, at the level of the tracheostome 15.

Figure 3:
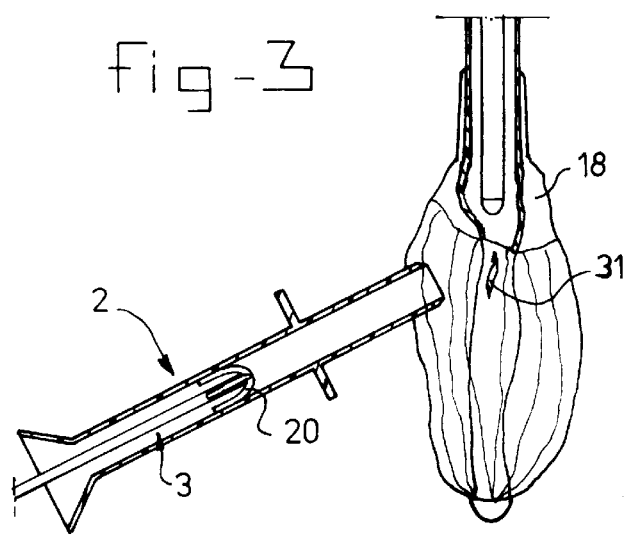
Figure 4:
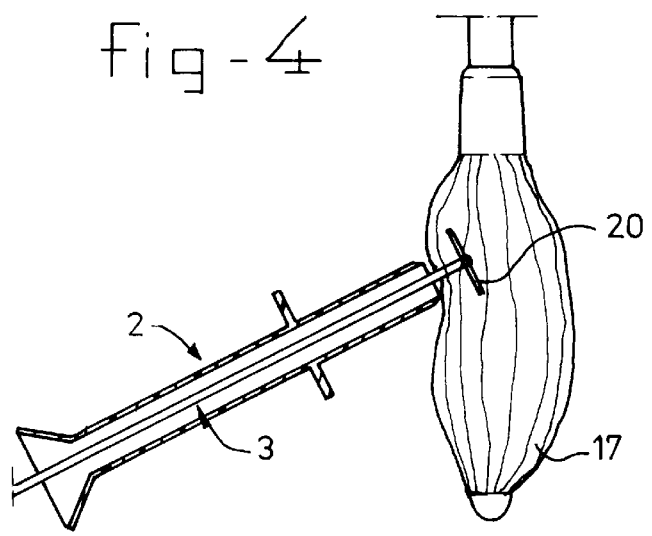

As is shown in FIG. 1, a hollow cutting element 2 or trocar is used to make the hole 16. The cutting portion of trocar 2 is shown on a larger scale in FIGS. 2 to 4. For reasons of clarity, the oesophagus and the trachea have not been drawn.

The trocar has a cutting edge 32, which extends to close to or between the thread-shaped reinforcing elements 17 which have been fitted in the expansion element 7. The flexible membrane 18 which forms a balloon and to which the grid of reinforcing threads 17 is attached can also be seen, partially in cross-section.

Figure 2:
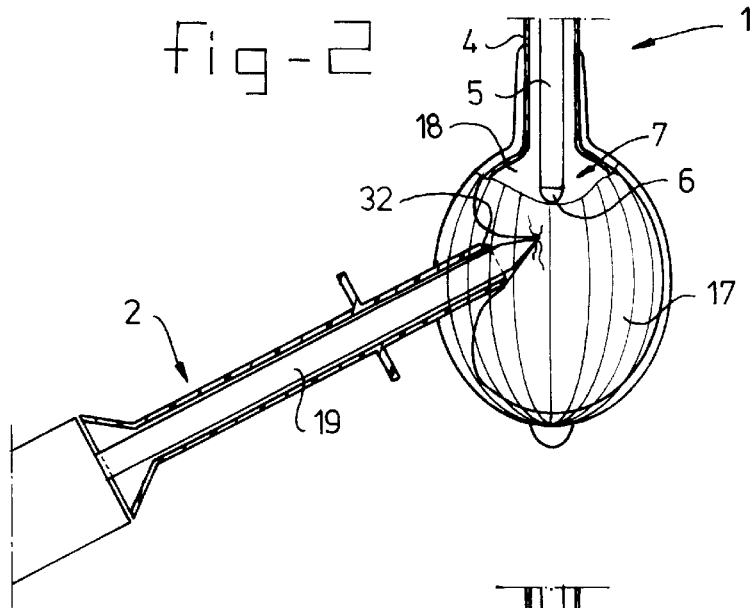
FIGS. 2 to 4 show various stages in the introduction of the guide element.

As is shown in FIG. 2, there is a separate cutting tool 19 in the trocar 2, with which cutting tool 19 the balloon 18 can be punctured if necessary. A hole 31 can then be produced in the balloon 18. The guide element 3 can have a number of, for example four, resilient, laterally extending arms 20. When pushed through the trocar 2 said arms 20 are resiliently bent backwards. In this state they end up behind the reinforcing threads 17 and remain hooked: see FIGS. 3 and 4.

As is shown in FIG. 5, the guide element 3 connected up in this way can then be pulled with the leader element 1 into the oesophagus 13, during which operation the guide element 3 is carried further and further into hole 16.

A dilator 21, to which a voice prosthesis is connected, is mounted on the end of the guide element 3. A few embodiments of the dilator are shown in FIGS. 6 and 7.

The dilator shown in FIG. 6, which, for example, can be connected via a screw fitting 22 to guide element 3, has a cavity 23 at its end, in which cavity a voice prosthesis 24 has been accommodated. Said voice prosthesis is shaped like a diabolo and has two flanges 25, 26, with a tubular section 27 between them. Flange 25 is clamped in cavity 23, whilst flange 26 protrudes beyond this.

As soon as the dilator 21 has been pulled via the hole 16 into the oesophagus 13, the flange 26 comes to lie around the outside of the hole 16.

At that point in time the voice prosthesis 24 is in the correct position and, by pulling the leader element 1 further out, while the voice prosthesis 24 is held by flange 26, flange 25 also comes free and then comes to lie against the inside wall of the oesophagus 13.

In the variant shown in FIG. 7 the dilator has an extension 28, which can be inserted into a hole 29 in a shank 30 of another known voice prosthesis. This voice prosthesis is not shown in more detail. The implantation of such a voice prosthesis, as, for example, shown in European Patent EP-B-507832, then proceeds in an identical manner.

What is claimed is:

1. Kit for the implantation of a voice prosthesis to restore the voice in a patient on whom a laryngectomy has been performed, comprising:

a leader element (1) which can be introduced via the mouth into the oesophagus (13) until a tip of the leader element is located close to the location where the voice prosthesis (24) is to be implanted, at which tip of said leader element first coupling means (17) are located, a hollow cutting element (2) for making a cut (16) in the wall (12) of the oesophagus at the level of the tracheostome (15), and a guide element (3), one end of which carries second coupling means (20) which, via the hollow cutting element which is located in the cut which has been made, can be brought into engagement with the first coupling means at the tip of the leader element, and the other end of which carries attachment means (21, 23) for attaching a voice prosthesis (24), which is to be implanted, to the guide element.

2. Kit according to claim 1, wherein the leader element has a light source (6) close to its tip.

3. Kit according to claim 1, wherein the leader element comprises an expansion element (7) which carries the first coupling means for coupling up the guide element.

4. Kit according to claim 3, wherein the expansion element is a balloon (18) which can be inflated via a tube provided in the leader element.

5. Kit according to claim 4, wherein the balloon has a grid of reinforcing elements (17) for attaching the second coupling means to the guide element.

6. Kit according to claim 5, wherein the guide element carries barb-shaped second coupling means which are folded together on insertion into the hollow cutting element (2), which second coupling means (20) can be inserted in the balloon (18) via the hollow cutting element and can then fold out such that they remain hooked into the balloon the grid.

7. Kit according to claim 1, wherein a dilator (21) is provided which at one end is connected to the guide element and at the other end has attachment means for the voice prosthesis for widening the cut when implanting a voice prosthesis attached to the dilator.

8. Kit according to claim 7, wherein the dilator is in the form of a cone, an apex (22) of which is connected to the guide element.

* * * * *